United States Patent
Jiang et al.

(10) Patent No.: US 9,995,660 B2
(45) Date of Patent: Jun. 12, 2018

(54) SMEAR STAINING MACHINE AND SMEARING CONTROL METHOD AND DEVICE THEREOF

(71) Applicant: SHENZHEN MINDRAY BIO-MEDICAL ELECTRONICS CO., LTD., Shenzhen (CN)

(72) Inventors: Bin Jiang, Shenzhen (CN); Tao Shen, Shenzhen (CN); Shubin Xue, Shenzhen (CN)

(73) Assignee: SHENZHEN MINDRAY BIO-MEDICAL ELECTRONICS CO., LTD., Shenzhen (CN)

( * ) Notice: Subject to any disclaimer, the term of this patent is extended or adjusted under 35 U.S.C. 154(b) by 0 days. days.

(21) Appl. No.: 15/271,089

(22) Filed: Sep. 20, 2016

(65) Prior Publication Data

US 2017/0010191 A1  Jan. 12, 2017

Related U.S. Application Data

(63) Continuation of application No. PCT/CN2014/073797, filed on Mar. 20, 2014.

(51) Int. Cl.
| | |
|---|---|
| *G01N 1/00* | (2006.01) |
| *G01N 1/28* | (2006.01) |
| *G01N 11/00* | (2006.01) |
| *G01N 11/04* | (2006.01) |
| *G01N 35/00* | (2006.01) |

(52) U.S. Cl.
CPC ........... *G01N 1/2813* (2013.01); *G01N 11/00* (2013.01); *G01N 11/04* (2013.01); *G01N 35/00029* (2013.01); *G01N 2035/00138* (2013.01)

(58) Field of Classification Search
CPC ...................................... G01N 35/10
See application file for complete search history.

(56) References Cited

U.S. PATENT DOCUMENTS

| 6,083,759 A | 7/2000 | Teshima |
| 2006/0065044 A1* | 3/2006 | Tsang ..................... G01N 11/06 73/54.07 |
| 2013/0021461 A1 | 1/2013 | Zahniser et al. |

FOREIGN PATENT DOCUMENTS

| CN | 101694431 A | 4/2010 |
| CN | 103175722 A | 6/2013 |
| CN | 103364236 | 10/2013 |

\* cited by examiner

*Primary Examiner* — Jyoti Nagpaul
(74) *Attorney, Agent, or Firm* — Kory D. Christensen; Polsinelli LLC

(57) ABSTRACT

A smear staining machine and a smearing control method and device thereof. The viscosity of the test sample is used for guiding the configuration of at least one smearing parameter. Because the viscosity of the test sample presents multiple influences of many effecting parameters, it is more suitable for presenting the characteristics of the test sample. Therefore, a better smearing effect could be acquired by referring the viscosity of the test sample to get the smearing parameter.

14 Claims, 5 Drawing Sheets

SMEAR STAINING MACHINE AND SMEARING CONTROL METHOD AND DEVICE THEREOF

TECHNICAL FIELD

The present disclosure relates to medical equipment, especially relating to a smear staining machine and a smear control method thereof.

BACKGROUND

The main function of a smear staining machine is for making a blood smear and staining the blood smear if a microscopic examination is needed when abnormal events are found after a routine examination. In the process of making a test sample into a blood smear for the microscopic examination, a blood film should be processed for forming a proper appearance with suitable thickness according to characteristics of the sample to configure smearing parameters such as blood drop, smearing speed or smearing angle.

At present, conventional smear technology adjusts smearing parameters mainly based on the HCT value of the sample. The HCT value is defined as the percentage of red blood cells in a certain volume of whole blood, also termed the "hematocrit." The hematocrit reflects characteristics of the blood sample in a certain perspective. It may look convenient, but some disadvantages appear as well at the same time, which are described below. Firstly, characteristics of the blood sample are not decided by the HCT value only. When the HCT value gets lower, the influence weight of the HCT value from characteristics of the sampling blood is more and more limited correspondingly.

On the other hand, blood plasma and internal suspended matter gradually become the main influence factors for characteristics of the blood sample. All kinds of environmental factors, such as environment temperature and humidity, storage period and preservation condition, influence the configuration of the blood film. For instance, by applying the same blood sample at the same smearing parameters, the blood film gets shorter and thicker when the environment temperature gets lower. On the contrary, the blood film gets longer and thinner when the environment temperature gets higher. In addition, the smear staining machine is designed to process abnormal samples, which usually come with a high percentage of low HCT value. Therefore, under the above conditions, the guiding function of the HCT value for the smear parameters would be reduced accordingly. Improper smear parameters may be acquired if smear parameters are adjusted in accordance with the HCT value so as to influence the effect of the blood film process.

SUMMARY

Therefore, a smear staining machine and a smearing control method and device are provided.

A smear control method for controlling a smear staining machine comprises determining at least one smearing parameter according to a viscosity of a test sample, and controlling a smear action according to the smearing parameter. Wherein determining at least one smearing parameter according to a viscosity of a test sample comprises: measuring a viscosity characteristic of the test sample when the test sample flows through a pipeline under a preset condition, wherein the viscosity characteristic is a physical quantity influenced by the viscosity of the test sample when the test sample flows, and the physical quantity is a function of viscosity; processing the viscosity characteristic of the test sample to generate a processing result; and determining the smearing parameter according to the processing result.

The viscosity of the test sample is used for guiding the configuration of at least one smearing parameter. Because the viscosity of the test sample presents multiple influences of many effecting parameters, it is more suitable for presenting the characteristics of the test sample. Therefore, a better smearing effect could be acquired by referring to the viscosity of the test sample to get the smearing parameter.

BRIEF DESCRIPTION OF THE DRAWINGS

For explaining embodiments of the present application or conventional technology more clearly, figures used for explaining embodiments or conventional background are introduced below. Obviously, in the drawings, similar drawings contain similar symbols for the same device or part, or for a part which has an analogous function and/or analogous structure. It should be understood that these drawings describe different kinds of embodiments, but are not to be considered as limitations of the scope.

DETAILED DESCRIPTION

Specific details for fully understanding each of the embodiments and being implemented by those skilled in the art are provided in the below description. However, it should be understood for those skilled in the art that the present invention is able to be implemented without the specific details as well. In some embodiments, conventional structures and functions are omitted to avoid confusion in the descriptions of the embodiments.

Unless it is acquired clearly under the context of the descriptions, the terms "comprise" and "include" should be defined as an opening definition but not a limited or an exhaustive definition.

Figure 1:
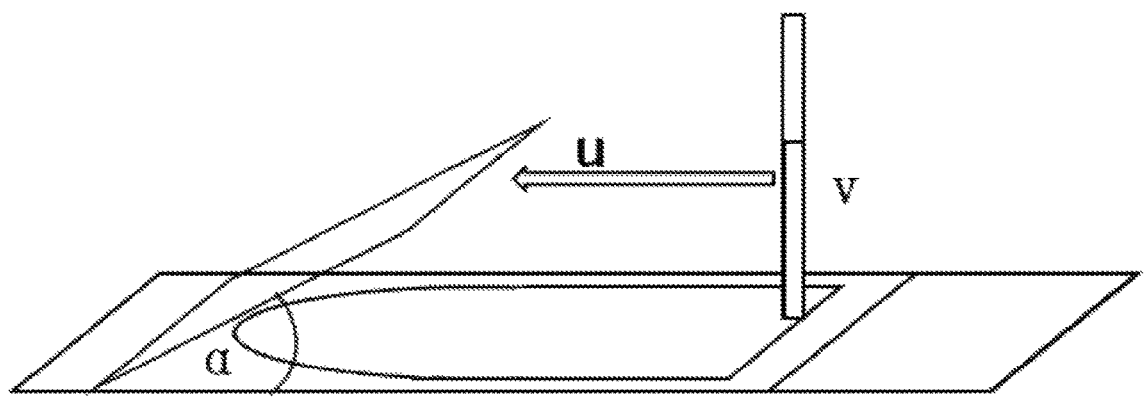
FIG. 1 is a schematic of a smearing process.

If a blood drop needs to be processed to form a blood smear whose appearance size (area of the blood film, width, length and appearance) and cell distribution under microscopic scale both satisfy a clinical trial, three main smearing parameters—volume of the blood drop (blood drop amount), smearing speed and smearing angle—must usually be selected. As illustrated in FIG. 1, thickness of the blood film is thicker and the blood film has a longer length (if with a fixed width) when the drop blood amount V is greater. The thickness of the blood film is thicker and the blood film is with shorter length when the smearing speed U is increased. The thickness of the blood film is thicker and the blood film is with shorter length when the smearing angle is increased.

In this application, when a smear staining machine makes blood smears, the smearing parameters are configured according to the viscosity of the blood sample. Except for the HCT value, the factors influencing the viscosity of a blood sample include size and form of the red blood cells, deformability of the red blood cells, aggregation of the red blood cells, amount of the white blood cells and platelets, blood plasma and polymer suspended matters inside it (all kinds of proteins, lipids, carbohydrates), sample temperature and storage period. In conclusion, the viscosity of a blood sample could be defined as the comprehensive effects of multiple factors. Therefore, the viscosity of a blood sample is more suitable for representing characteristics of the sampling blood.

The apparent viscosity of fluid could generally reflect the viscosity of fluid. Therefore, in one embodiment, the apparent viscosity of the blood sample could be examined under conventional technologies. The apparent viscosity of the blood sample is applied to guide the configuration of the smearing parameters then the smearing process is controlled according to the smearing parameters. However, examination of the apparent viscosity of the blood sample is complex, and usually can only be implemented by adding additional examination equipment. In addition, the operation period for waiting for the examining result of the apparent viscosity of the blood sample would be quite long correspondingly, so that the viscosity of the blood sample could easily be influenced by the factors of temperature and aging sample. It means the temperature in examining the apparent viscosity of the blood sample may not be the same with the temperature in sample smearing. So, the apparent viscosity of the blood sample may not be the same with the apparent viscosity in sample smearing as well.

In one embodiment of this application, relative viscosity or viscosity ratio of the tested samples is applied to guide the configuration of the smearing parameters. Relative viscosity of the tested sample is defined as the viscosity of the tested sample referring to a preset viscosity of a reference fluid under a smearing temperature. In this application, the temperature at the time point the relative viscosity of the tested sample is calculated is defined as the smearing temperature. The viscosity ratio is the viscosity ratio between the tested sample and the reference fluid. If a user wants to calculate the relative viscosity or the viscosity ratio of the tested samples, at least one reference fluid should be selected at first. After that, the relative viscosity or the viscosity ratio of the tested samples could be calculated by examining the tested samples and the reference fluid under the same conditions.

The below descriptions disclose a method for guiding the configuration of the smearing parameters by applying the relative viscosity or viscosity ratio of the tested samples.

Figure 2:
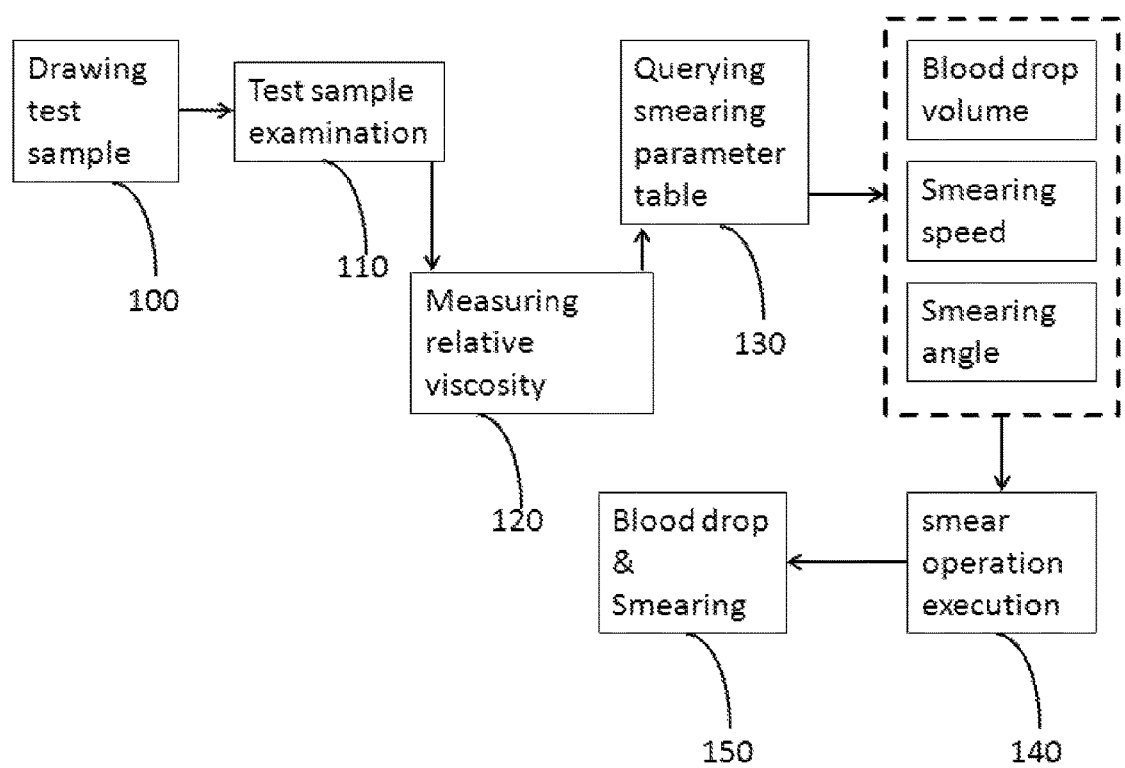
FIG. 2 is a flowchart of the smearing process in one embodiment of the present application.

After the reference fluid is determined, apparent viscosities of the reference fluid in various temperatures could be acquired at first. When the smearing process is needed, the flowchart of the smearing process is shown as FIG. 2, including the steps below:

Step 100, drawing the test sample. Step 110, examining the test sample under the same conditions compared to the reference fluid. The examination of the reference fluid should be preferably conducted before the examination of the test sample, which means the examination of the reference fluid should be conducted before Step 100.

Step 120, comparing a test result of the test sample with a test result of the reference fluid so as to acquire the viscosity ratio of the test sample relative to the reference fluid. After that, based on the apparent viscosity of the reference fluid under the test temperature, calculating the relative viscosity of the test sample. The viscosities of the reference fluid in various temperatures could be acquired by pre-testing or pre-querying.

Step 130, determining the smearing parameters according to the relative viscosity of the test sample. The smearing parameters mainly include blood drop amount, smearing speed and smearing angle. The smearing parameters could be acquired by the way of a querying table, relation curves or calculation equations. According to experiments, the larger the relative viscosity of the test sample is, the more difficult it is to process the blood film accordingly. It requires a lower smearing speed and a smaller smearing angle. Under this principle, such as throughout experiments for massive samples, a corresponding table between the relative viscosity and the smearing parameters is acquired. If the relative viscosity of the tested sample being examined is determined, the smearing parameters suitable for this tested sample could be acquired by checking the corresponding table.

Step 140, controlling a smearing mechanism according to the smearing parameters.

Step 150, dropping the test sample on a slide and extending the test sample as a film by the smearing mechanism according to the smearing parameters.

Because the reference fluid is determined, the relative viscosities of it under various temperatures could be pre-acquired as well. Because temperature influences have already been considered in the examination process for the calculation of the apparent viscosity of the reference fluid, the relative viscosity of the test sample referring to the viscosity ratio between the reference fluid and the test sample has been considered and avoided the temperature influences as well. In addition, because the relative viscosity of the test sample is examined only when a smearing process is required, the time gap between the examination for the relative viscosity and the smearing process would be small enough so that the relative viscosity in the examination could be more precisely close to the relative viscosity of the test sample when it is smeared. The above embodiment eliminates the influences of multiple factors such as environment temperature and sample storage period.

Figure 3:
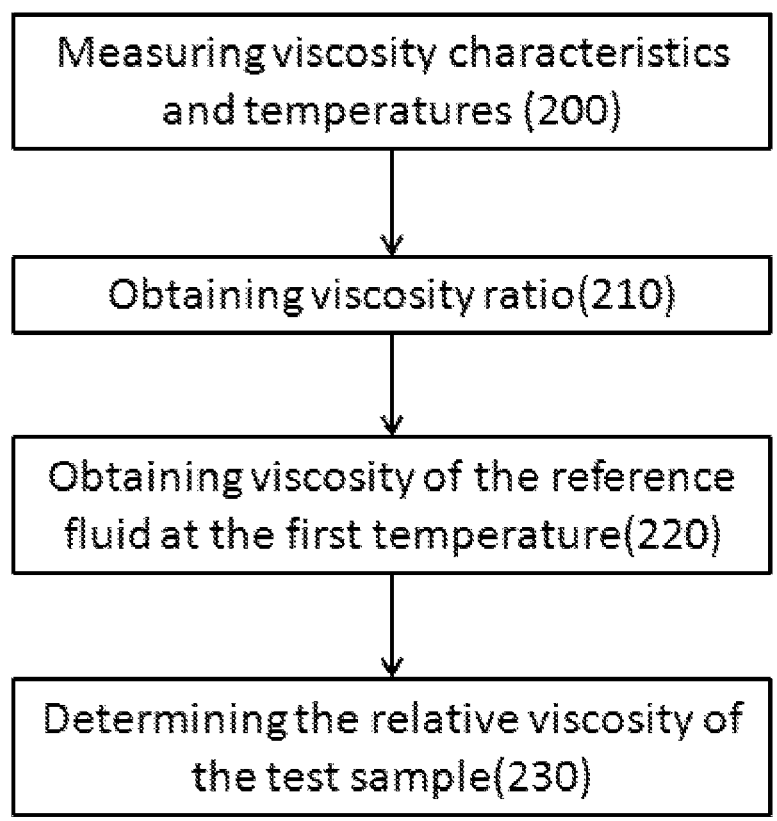
FIG. 3 is a measuring flowchart of the relative viscosity of a test sample in one embodiment of the present application.

For measuring the relative viscosity of the test sample, a factor called "viscosity characteristic" is defined in the embodiments of this application. The viscosity characteristic is defined as a physical quantity influenced by the viscosity of materials when the materials flow in a medium. The physical quantity could be represented as a functional equation of viscosity. The flow chart for calculating the relative viscosity of the test sample is shown in FIG. 3, including the below steps:

Step 200, measuring the temperature and the viscosity characteristic. In Step 200, the viscosity characteristic of the reference fluid and the test sample are respectively examined when the reference fluid and the test sample flow through a pipeline under the same conditions. A first temperature, defined as the temperature of the examination for the reference fluid, is examined at Step 200 at the same time. When the viscosity characteristic of the reference fluid is calculated, the reference fluid should flow through the pipeline under a preset configuration. When the viscosity characteristic of the test sample is calculated, the test sample should flow through the pipeline under the preset configuration the same as conducting the viscosity characteristic of the reference fluid. The preset configuration could include a configured flow rate, velocity or volume. The pipeline for calculating the viscosity characteristic of the test sample or the reference fluid could be an identical pipeline or different physical pipelines with the same geometric size preferably.

Step 210, comparing the viscosity characteristic of the reference fluid with the viscosity characteristic of the test sample to acquire the viscosity ratio between the reference fluid and the test sample.

Step 220, acquiring the apparent viscosity of the reference fluid under the first temperature.

Step 230, calculating the viscosity of the test sample according to the functional equation of the viscosity ratio and the apparent viscosity of the reference fluid, and defining the above viscosity as the relative viscosity of the test sample.

A detailed description of an example for defining the viscosity characteristic as a pressure difference is disclosed below:

Embodiment 1

The smear staining machine includes a sampling mechanism, a smearing mechanism and a processor. The sampling mechanism is implemented for drawing or discharging fluids. The smearing mechanism is implemented for dropping a test sample on a slide and extending the test sample as a film according to the smearing parameters. The processor respectively connects to the sampling mechanism and the smearing mechanism for controlling the operations of the sampling mechanism and the smearing mechanism individually. In this application, the processor also acquires the smearing parameters according to the viscosity of the test sample, and controls the smear operation of the smearing mechanism according to the smearing parameters.

The viscosity of the test sample could be inputted into the smear staining machine by the user after the viscosity of the test sample is acquired outside the smear staining machine. For example, an examining method could be applied for acquiring the apparent viscosity of the test sample at first. Then the apparent viscosity of the test sample is inputted into the smear staining machine. The processor processes the above inputted information and selects the smearing parameters according to the inputted apparent viscosity.

In one embodiment, when smear is required, a mechanism of the smearing mechanism itself is implemented for measuring the viscosity of the test sample. The sampling mechanism includes a sample pipeline, an injector and a detector. The detector is configured on the sample pipeline for measuring the viscosity characteristic of the test sample when the test sample flows through the sample pipeline under the preset configuration. The processor measures the viscosity characteristic outputted from the detector and processes the viscosity characteristic to produce a processing result. The processor further determines the smearing parameters in accordance with the processing result.

Figure 4:
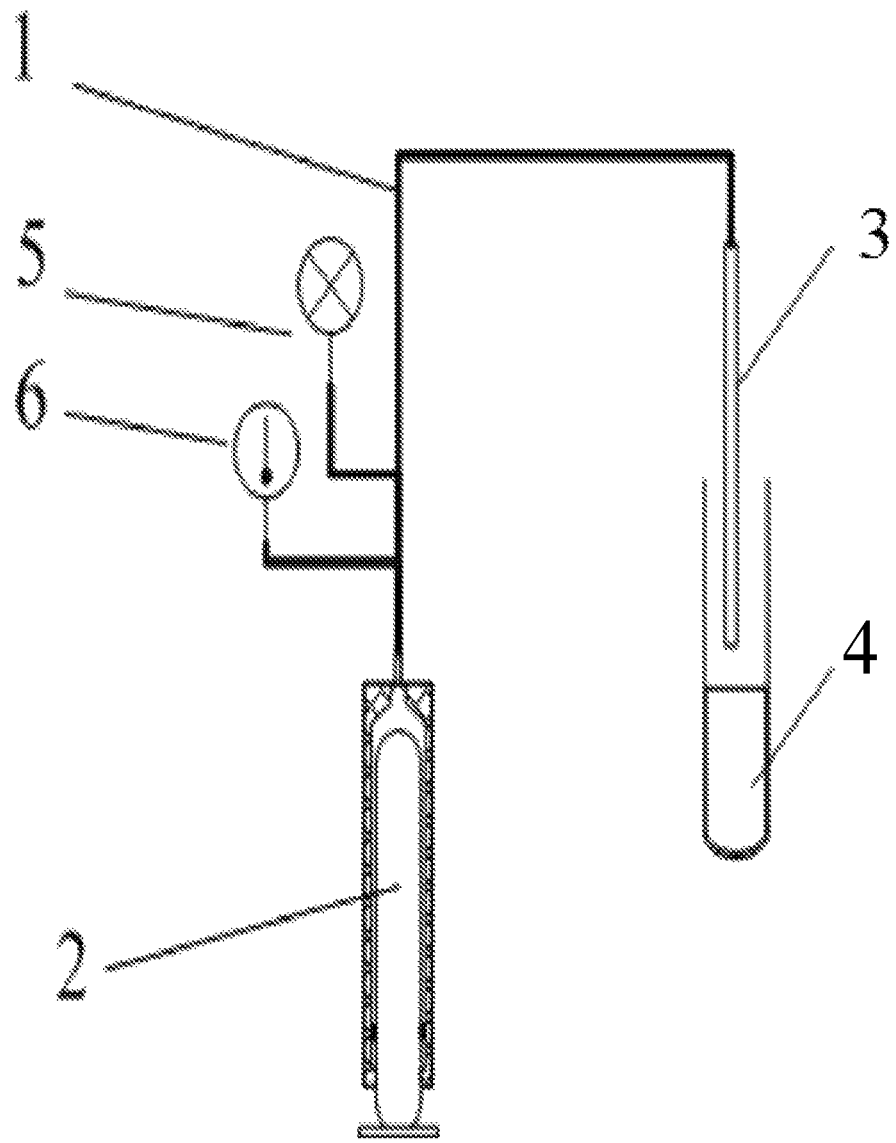
FIG. 4 is a structure schematic of one device embodiment of the present application.

FIG. 4 illustrates a structure diagram of the sampling mechanism. In this embodiment, a pressure sensor is implemented as a detector for measuring the viscosity characteristic. Under this configuration, the viscosity characteristic is represented as pressure data. The sampling mechanism includes a sample pipeline 1, an injector 2, a sample pin 3, a pressure sensor 5, a temperature sensor 6 and a processor. An outlet of the injector 2 is coupled with a first terminal of the sample pipeline 1. A second terminal of the sample pipeline 1 is coupled with the sample pin 3. The sample pin 3 is implemented for drawing a sample from a test tube 4. The pressure sensor 5 and the temperature sensor 6 are configured on the sample pipeline 1 respectively. For instance, the pressure sensor 5 and the temperature sensor 6 are able to be configured near the first terminal or a middle portion of the sample pipeline 1. The pressure sensor 5 and the temperature sensor 6 are implemented for measuring the pressure state and the temperature state in the pipeline 1 respectively. The processor electrically couples to the injector 2 for controlling the injector 2 to drive a drawing operation or a discharging operation of the sample pipeline 1.

Moreover, the processor calculates the viscosity ratio between the reference fluid and the test sample according to the pressure data and the temperature data measured by the pressure sensor 5 and the temperature sensor 6, and further calculates the relative viscosity of the test sample correspondingly. The smearing parameters are acquired thereafter according to the viscosity of the test sample. The smearing machine is controlled for smearing under acquired smearing parameters. In one embodiment, liquid material is generally selected as the reference fluid. For ensuring the accuracy of the sampling process, the sample pipeline and the injector are demanded to preserve some liquid inside under normal circumstances. In the meantime, the liquid inside the injector and the pipeline is required to select from an isosmotic solution for avoiding the transformation that happens when the red blood cells engage with the liquid material. Under this situation, for the convenience of calculation, the reference fluid includes reference liquid and reference gas. In one of the below embodiments, an isosmotic solution is selected as the reference liquid. The detailed test process is disclosed below:

1. calibration process 1: the injector 2 controls the sample pipeline 1 to draw air with the same volume compared with the sample drawn in the above sample drawing process and with the same speed as in the above sample drawing process. The pressure sensor 5 and the temperature sensor 6 respectively measure the pressure data and the temperature data in the sample pipeline 1 when the injector 2 draws air. The pressure data and the temperature data are recorded in the above process. In this embodiment, the pressure data outputted from the pressure sensor 5 is relative pressure data. More precisely, the pressure data outputted from the pressure sensor 5 is the pressure difference relative to the atmospheric pressure of the environment.

2. calibration process 2: the injector 2 controls the sample pipeline 1 to draw an isosmotic solution with the same volume compared with the sample drawn in the above sample drawing process and with the same speed as in the above sample drawing process. The pressure data and the temperature data are recorded in the above process.

3. calculation process: the injector 2 controls the sample pipeline 1 to draw the sample. The pressure data and the temperature data are recorded in the above process as well.

Figure 5:
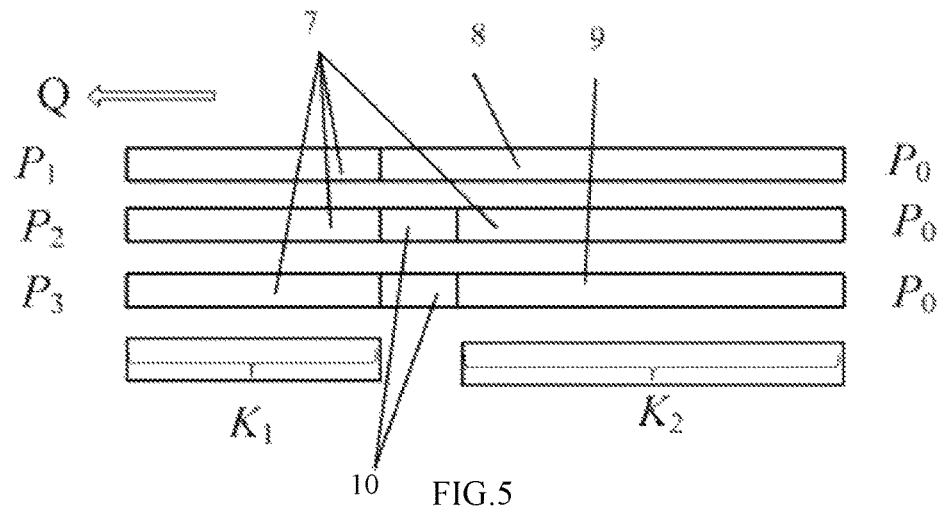
FIG. 5 is a schematic illustrating states in a pipeline during the relative viscosity measuring process in one embodiment of the present application.

4. Acquiring three pipeline pressure data during the above three processes all at the same specific time point, wherein the gas pressure difference is marked as $\Delta P_1$, the liquid pressure difference is marked as $\Delta P_2$ and the pressure difference in the sample acquiring process is marked as $\Delta P_3$. In other embodiments, if outputs of the pressure sensor are absolute pressure values, the pressure difference between the absolute pressure value in the air drawing process (calibration process 1) and the environment atmospheric pressure P0 is defined as $\Delta P_1$. Under the same rule, the pressure difference between the absolute pressure value in the liquid drawing process (calibration process 2) and the environment atmospheric pressure P0 is defined as $\Delta P_2$, and the difference between absolute pressure of sampling process and the environment atmospheric pressure P0 is defined as $\Delta P_3$. The state of the pipeline at the specific time point is shown in FIG. 5. In FIG. 5, 7 represents the isosmotic solution in the pipeline, 8 is the air sample in the pipeline, 9 is the sample in the pipeline and 10 is an isolated air gap.

If the time points between the calculation process and the examination process are close to each other enough, the temperature values of the calculation process and the examination process could be defined as identical. Under the above conditions, the relation equations of $\Delta P_1$, $\Delta P_2$ and $\Delta P_3$ could be defined from the below equations (1), (2) and (3):

$$\Delta P_1 = \eta_D \cdot Q \cdot K_1 \tag{1}$$

$$\Delta P_2 = \eta_D - Q - \kappa_1 + \eta_D - Q - \kappa_2 \tag{2}$$

$$\Delta P_3 = \eta_D - Q - K_1 + \eta_B - Q - K_2 \tag{3}$$

Where $\eta_B$ is the relative viscosity of the test sample, $\eta_D$ is the relative viscosity of the reference liquid at the first temperature, Q is the flow rate of the liquid flowing in the pipeline, $K_1$ is the damping value of the front portion of the pipeline, and $K_2$ is the damping value of the backend portion of the pipeline. The main factors influencing the damping value only relate to the pipeline features, such as pipeline length, pipeline radius, etc. $\Delta Pi$ is the pressure difference of the reference gas, $\Delta P_2$ is the pressure difference of the reference liquid and $\Delta P_3$ is the pressure difference of the test sample.

For equation (1) into equation (2), and comparing equation (2) with equation (3), equation (4) is acquired as below:

$$\eta_S = \frac{AP_3 - AP_1}{AP_2 - AP_1} \cdot \eta_D \tag{4}$$

By acquiring $\eta_D$, the relative viscosity of the test sample $\eta_B$ could be calculated according to equation (4).

In the above embodiments of this application, by comparing a known viscosity of the reference fluid with an unknown viscosity of the test sample, the relative viscosity of the test sample relating to the known viscosity of the reference fluid in the real time temperature is calculated. For implementing the above solution, no additional detection equipment is required in hardware approaches, but only a temperature sensor and a pressure sensor are added in the original smear machine. By using the data detected from the pressure sensor and the temperature sensor, the relative viscosity of the test sample could be calculated. In addition, when the smear machine stays at a constant temperature environment, there is no need to add the temperature sensor with the sampling mechanism, as the environment temperature of the smear machine could be obtained from an additionally provided thermometer. The apparent viscosity of the reference liquid is acquired according to the environment temperature. In this embodiment, the time point of the viscosity measurement of the test sample is close to the time point of the smear. Moreover, both of the above measurements are implemented at a similar position in the smear machine so that the temperatures of both are close or identical to each other. Under this circumstance, the measured viscosity of the test sample could represent the true viscosity of the test sample more identically.

Embodiment 2

In actual practice, execution of the above calibration processes may not be expected by the user in every smearing process. Therefore, measuring the reference liquid could be conducted first to execute the calibration process, and the measuring result of the above is saved correspondingly. In the situation that the temperature of the isosmotic solution during the calibration process is different from the temperature of the isosmotic solution during the calculation process, the responding process for that is described below:

The processes for measuring pressure and temperature are the same as with Embodiment 1. Equations (1), (2) and (3) should be amended to equations (5), (6) and (7) accordingly as shown below:

$$\Delta P_{1\_T1} = \eta_{o\_T1} \cdot Q \cdot K_1 \tag{5}$$

$$\Delta P_{2\_T1} = \eta_{D\_T1} \cdot Q \cdot K_1 + \eta_{D\_T1} \cdot Q \cdot K_2 \tag{6}$$

$$\Delta P_{1\_T1} \frac{\eta_{D\_T2}}{\eta_{D\_T1}} = \eta_{D\_T2} \cdot Q \cdot K_1 \tag{7}$$

In equations (5), (6), and (7), T1 is defined as the temperature of the isosmotic solution during the calibration process. T2 is defined as the temperature during the measuring of the test sample. $\Delta P_{1\ \ldots\ T1}$ is defined as the pressure difference of the pipeline and the environment pressure in the air drawing process during calibration (when temperature is defined as T1). $\Delta P_{2\ \ldots\ T1}$ is defined as the pressure difference of the pipeline and the environment pressure when drawing the isosmotic solution during calibration (when temperature is defined as T1). $\Delta P_{3\ \ldots\ T2}$ is defined as the pressure difference of the pipeline and the environment pressure during calibration (when temperature is defined as T2).

Equation (5) and equation (6) should be calibrated in accordance with the temperature data from Step 1 and Step 2. The result of the above calibration is shown in equation (8) and equation (9):

$$\Delta P_{1\_T1} \frac{\eta_{D\_T2}}{\eta_{D\_T1}} = \eta_{D\_T2} \cdot \rho \cdot K_1 \tag{8}$$

$$\Delta P_{2\_T1} \frac{\eta_{D\_T2}}{\eta_{D\_T1}} = \eta_{D\_T2} \cdot Q \cdot K_1 + \eta_{D\_T2} \cdot \rho \cdot K_2 \tag{9}$$

For equation (8) into equation (9), and comparing equation (9) with equation (7), equation (10) is acquired as below:

$$\eta_B = \frac{\eta_{D\_T1} \Delta P_3 - \eta_{D\_T2} \Delta P_1}{\Delta P_2 - \Delta P_1} \tag{10}$$

For the situation where the drawing pipeline and the time period of the examination process are both longer, the temperatures of the isosmotic solution in different portions of the pipeline could be different. By implementing the solution of this embodiment, the relative viscosity of the test sample calculated could more precisely represent the true viscosity of the test sample at the present temperature.

By implementing this embodiment, because the characteristics of the reference liquid are confirmed, the calibration process could be conducted as previously. Therefore, the pressure data of the reference liquid is measured and saved before the viscosity is measured. When the smearing process is acquired, the drawing process is conducted correspondingly. By using the pressure data measured during the sample drawing process and the pressure data of the reference liquid measured before cooperatively, the viscosity of the test sample in the present temperature could be calculated without an additional viscosity calculation process.

In accordance with the disclosed content and physical invention of this embodiment, the reference liquid mentioned could be a different liquid compared with the pre-stored liquid. By implementing the measurement method and inventive idea, the relative viscosity of the test sample can be calculated.

Embodiment 3

In this embodiment, the calibration process and the calculation process are conducted in the meantime, or are conducted in sequence during a narrow time period. Therefore, the difference of environment temperatures between the above two processes is small enough and could be considered as identical. The relative viscosity then could be simplified as below:

$$\frac{\eta_B}{\eta_D} = \frac{\Delta P_3 - \Delta P_1}{\Delta P_2 - \Delta P_1} \quad (11)$$

Thereafter, according to $$\frac{\eta_B}{\eta_D},$$

by using the preset relations between the viscosity ratio and the smearing parameters in different temperatures, the smearing parameters under the present environment temperature is acquired according to the conducted viscosity ratio. The environment temperature is the temperature where the smearing machine is positioned, which could be measured by the temperature sensor on the smearing machine or by another individual thermometer.

Accordingly, the smearing machine in this embodiment includes a parameter determination module and a control module. The parameter determination module is implemented for confirming the smearing parameters according to the viscosity of the test sample. The control module is implemented for controlling the smearing machine to smear according to the smearing parameters. The parameter determination module includes a viscosity calculation unit and a parameter determination unit. The viscosity calculation unit is implemented for calculating the relative viscosity of the test sample. The relative viscosity of the test sample is defined as the apparent viscosity of the test sample relative to a known viscosity of the reference liquid at the smearing temperature. The parameter determination unit confirms the smearing parameters according to the relative viscosity.

Figure 6:
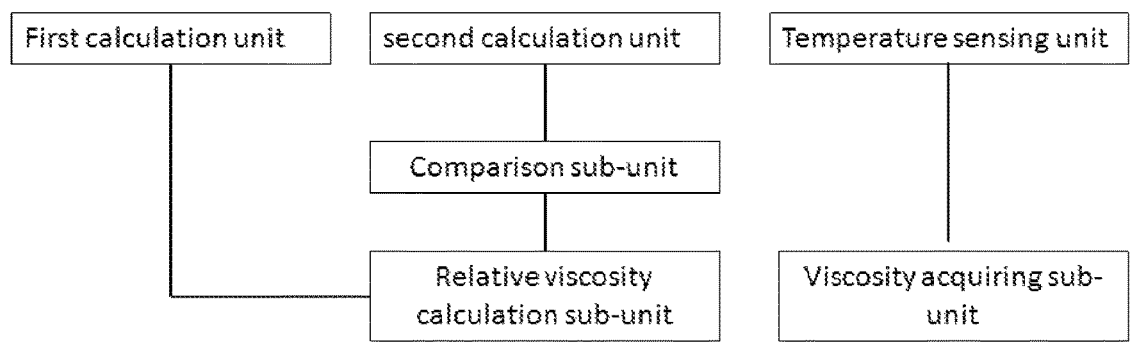
FIG. 6 is a structure schematic of a viscosity measuring unit in one embodiment of the present application.

As shown in FIG. 6, the viscosity calculation unit includes a first calculation sub-unit 11, a temperature receiving sub-unit 12, a second calculation sub-unit 13, a comparison sub-unit 14, a viscosity acquiring sub-unit 15 and a relative viscosity calculation sub-unit 16. The first calculation sub-unit 11 is implemented for calculating a viscosity characteristic of the reference liquid when the reference liquid flows through the pipeline under a preset condition. The viscosity characteristic is defined as a physical quantity influenced by the viscosity of the reference liquid when the liquid flows. The physical quantity could be represented as a function formula of the viscosity.

The temperature receiving sub-unit 12 is implemented for measuring temperatures of the pipeline from the temperature sensor, which includes a first temperature during the measurement of the reference liquid and/or a second temperature during the measurement of the test sample. The second calculation sub-unit 13 is implemented for calculating the viscosity characteristic of the test sample when the test sample flows through the pipeline under a preset condition. The comparison sub-unit 14 is implemented for comparing the viscosity characteristic of the test sample with the viscosity characteristic of the reference liquid to acquire a relation with the ratio viscosity between the reference liquid and the test sample. The viscosity acquiring sub-unit 15 is implemented for acquiring the apparent viscosity of the reference liquid at the first temperature. The relative viscosity calculation sub-unit 16 is implemented for calculating the viscosity of the test sample according to the ratio viscosity relation and the viscosity of the reference liquid, and defining the acquired viscosity as the relative viscosity of the test sample.

At the condition that the viscosity characteristic is defined as pressure data, the first calculation sub-unit 11 is implemented for measuring the pressure difference of the pipeline measured by the pressure sensor when the reference liquid flows through the pipeline under the preset flow rate. The second calculation sub-unit 13 is implemented for measuring the pressure difference of the pipeline measured by the pressure sensor when the reference test sample flows through the pipeline under the preset flow rate. In other words, the second calculation sub-unit 13 controls the sampling pipeline to draw the reference fluid and the test sample with a same volume such that the reference fluid and the test sample flow through the pipeline in a same amount.

If there is pre-stored liquid left in the pipeline and the reference fluid includes reference gas and reference liquid, the pressure data should include the pressure difference of the pipeline measured by the pressure sensor when the reference gas flows through the pipeline under the preset flow rate and the pressure difference of the pipeline measured by the pressure sensor when the reference liquid flows through the pipeline under the preset flow rate.

When the temperature difference between the calibration process and the calculation process is ignored, the relative viscosity of the test sample is calculation through the below equation:

$$\eta_B = \frac{AP_3 - AP_1}{AP_2 - AP_1} \cdot \eta_D$$

Wherein $\eta_B$ is the relative viscosity of the test sample, $\eta_D$ is the viscosity of the reference liquid under the first temperature, $\Delta pi$ is the pressure difference of the reference gas, $\Delta P_2$ is the pressure difference of the reference liquid, and $\Delta P_3$ is the pressure difference of the test sample.

If the temperature difference between the calibration process and the calculation process is considered, the relative viscosity of the test sample is calculation through the below equation:

$$\eta_B = \frac{\eta_{D\_T1} AP_3 - \eta_{D\_T2} AP_1}{AP_2 - AP_1}$$

Wherein $\eta_B$ is the relative viscosity of the test sample, $\eta_{D\_T1}$ is the apparent viscosity of the reference liquid under the first temperature, $\eta_{D\_T2}$ is the apparent viscosity of the reference liquid under the second temperature, is the pressure difference of the reference gas, $\Delta P_2$ is the pressure difference of the reference liquid, and $\Delta P_3$ is the pressure difference of the test sample.

When the smearing machine is positioned in a constant temperature environment, there could be no temperature sensor on the sampling mechanism. The environment temperature of where the smearing machine is positioned could be provided from an additional thermometer and the apparent viscosity of the reference liquid is acquired under the environment temperature.

In accordance with the public content of this application, those skilled in the art should understand that the viscosity calculation unit could further calculate the viscosity ratio between the test sample and the reference liquid according to the feature quantities of the test sample and the reference liquid when the test sample and the reference liquid flow through the pipeline under the same configuration. The parameter determination unit confirms the smearing parameters according to the viscosity ratio. In this circumstance, the environment temperature of the smearing machine is generally required, and the smearing parameters are acquired through table check, relation curve check or equation calculation according to the viscosity ratio and the environment temperature.

The pressure data, for instance, in this application is the pressure data acquired from a test tube in a sampling process. Otherwise, pressure data under other flowing states which represent the data when a blood sample flows through the pipeline is also acceptable. That data above includes but is not limited to the data pressure under a transportation process, a dividing process or a discharging process.

In the embodiments in this application, the injector is implemented for sample drawing under a fixed flow rate. However, other devices are also acceptable for getting a fixed flow rate, such as a rotary piston pump or a peristaltic pump. A flow rate varied under a particular regularity could be used, such as linearly increasing the flow rate from 0 to 300 uL/s.

In accordance with the publishing content and inventive idea of the present application, it should be understood by the skilled in the art that the viscosity characteristic in this application could be replaced by other physical quantities, such as velocity. For example, one or more light sensors could be added to configure in one or some specific positions in the sampling pipeline so that a time period defined as a period that the blood sample flowing through the above light sensors in the sampling process could be measured. Specifically, as shown in FIG. 5, a time point when the $K_2$ section of the blood sample or the head portion of diluents trigger an opto-couple reaction could be measured for velocity measurement. Or, a time point when the tail portion triggers an opto-couple reaction could be measured for velocity measurement as well. Because deformation could happen on the pipeline under over-pressure and the pressure difference generated on the sampling process would become larger when the viscosity increases, the deformation of the pipeline would be increased correspondingly when the viscosity increases to over-pressure so as to make a blood sample with more viscosity take more time to reach one of the light sensors from the beginning of the sampling process. Or, the blood sample with more viscosity has to take more time to flow through one light sensor from another in the sampling process. The above effect could be used to calculate the viscosity of the blood sample. Precisely, the relation between the viscosity and the time difference could be calculated at first, then back calculate the viscosity according to the above relation in real practice.

The examples in this application are for blood samples. However, other liquid samples are also suitable for processing by the smearing method and machine disclosed in this application, such as serum samples or body fluid samples.

In this application, air and an isosmotic solution are selected to be drawn in the calibration process. But air could be replaced by other gases because some examinations have to be conducted under an anaerobic environment. The isosmotic solution also could be replaced by other reagents for processing other functions in the smearing machine. For example, deionized water, rhenate buffer, alcohol and dye liquid are all needed for the smearing machine in the dying process.

Various advantages may be realized based on the above-described approaches.

1. Simple structure: The original sampling mechanism of the smearing machine is reserved. Only an additional pressure sensor and an additional temperature sensor are required.
2. No additional operation of viscosity calculation is required; the pressure data acquired in the sampling process by the sampling mechanism could be implemented directly.
3. No additional calibrating materials or control materials are required. The viscosity of the isosmotic solution is configured as a standard base for the smearing machine.

It is understandable for those skilled in the art that all or some of the processes disclosed in the embodiments of the present application are able to be implemented by instructing relating hardware through computer programs. The above programs are able to be stored in readable storing media of a computer. The above programs are able to include the implementation of all flow charts for all methods disclosed in the above embodiments in execution. The readable storing media include but are not limited to hard disc, optical disc, read-only memory (ROM) and random access memory (RAM).

Although the present disclosure has been described through specific embodiments, the present disclosure is not limited to the specific embodiments described above. Those of skill in the art should understand that various modifications, alternatives and variations may be made based on the present disclosure, which all should be within the scope of protection of the present disclosure. Furthermore, "a (an) embodiment" or "another embodiment" mentioned above may represent different embodiments, or may also be combined completely or partly in one embodiment.

The invention claimed is:

1. A smear control method for controlling a smear staining machine, comprising:
    determining at least one smearing parameter according to a viscosity of a test sample comprises: measuring a viscosity characteristic of the test sample when the test sample flows through a pipeline under a preset condition, wherein the viscosity characteristic is a physical quantity influenced by the viscosity of the test sample when the test sample flows, and the physical quantity is a function of viscosity; and
    controlling a smear action according to the smearing parameter;
    wherein the viscosity characteristic of the test sample is a pressure comprising an absolute pressure or a pressure difference relative to an atmospheric pressure.

2. The smear control method of claim 1, wherein the determining at least one smearing parameter further comprises:

processing the viscosity characteristic of the test sample to generate a processing result; and determining the smearing parameter according to the processing result.

3. The smear control method of claim 2, further comprising:

determining the smearing parameter according to a relative viscosity of the test sample, wherein the relative viscosity of the test sample is a viscosity of the test sample relative to a known apparent viscosity of a reference fluid at a smearing temperature, and wherein processing the viscosity characteristic of the test sample comprises:

comparing the viscosity characteristic of the test sample with a viscosity characteristic of the reference fluid when the reference fluid flows through the pipeline under the same preset condition to generate a comparison result; and calculating the viscosity of the test sample according to the comparison result and the known apparent viscosity of the reference fluid and using the viscosity calculated as the relative viscosity of the test sample.

4. The smear control method of claim 3, further comprising:

according to the relative viscosity, determining the smearing parameter using a table, a curve or a formula.

5. The smear control method of claim 3, further comprising:

while measuring the viscosity characteristic of the reference fluid when the reference fluid flows through the pipeline under the same preset condition, measuring a first temperature in the pipeline; and wherein the viscosity of the reference fluid is an apparent viscosity of the reference fluid at the first temperature.

6. The smear control method of claim 5, further comprising:

while measuring the viscosity characteristic of the test sample when the test sample flows through the pipeline under the preset condition, measuring a second temperature in the pipeline.

7. The smear control method of claim 6, wherein the viscosity characteristic of the test sample or the viscosity characteristic of the reference fluid is a pressure difference, and the reference fluid comprises a reference gas and a reference liquid when there is a liquid preserved in the pipeline, and the relative viscosity of the test sample is calculated through the below equation:

$$\eta_B = \frac{\eta_{D\_T1} \Delta P_3 - \eta_{D\_T2} \Delta P_1}{\Delta P_2 - \Delta P_1}$$

where $\eta_B$ is the relative viscosity of the test sample, $\eta_{D\_T1}$ is a viscosity of the reference liquid at the first temperature, $\eta_{D\_T2}$ is a viscosity of the reference liquid at the second temperature, $\Delta P_1$ is a pressure difference of the reference gas, $\Delta P_2$ is a pressure difference of the reference liquid, and $\Delta P_3$ is a pressure difference of the test sample.

8. The smear control method of claim 5, wherein the viscosity characteristic of the test sample or the viscosity characteristic of the reference fluid is a pressure difference, and the reference fluid comprises a reference gas and a reference liquid when there is a liquid preserved in the pipeline, and the relative viscosity of the test sample is calculated through the below equation:

$$\eta_B = \frac{\Delta P_3 - \Delta P_1}{\Delta P_2 - \Delta P_1} \cdot \eta_D$$

where $\eta_B$ is the relative viscosity of the test sample, $\eta_D$ is a viscosity of the reference liquid at the first temperature, $\Delta P_1$ is a pressure difference of the reference gas, $\Delta P_2$ is a pressure difference of the reference liquid, and $\Delta P_3$ is a pressure difference of the test sample.

9. The smear control method of claim 3, wherein the pipeline is a sampling pipeline of a smear staining machine, and where the method further comprises:

controlling the sampling pipeline to draw the reference fluid and the test sample with a same volume such that the reference fluid and the test sample flow through the pipeline in a same amount.

10. The smear control method of claim 3, wherein the viscosity characteristic of the test sample or the viscosity characteristic of the reference fluid is a velocity.

11. The smear control method of claim 2, further comprising:

determining the smearing parameter according to a viscosity ratio between the test sample and a reference fluid; and wherein processing the viscosity characteristic of the test sample comprises:

comparing the viscosity characteristic of the test sample with a viscosity characteristic of the reference fluid when the reference fluid flows through the pipeline under the same preset condition to obtain the viscosity ratio between the test sample and the reference fluid.

12. The smear control method of claim 11, further comprising:

while measuring the viscosity characteristic of the test sample when the test sample flows through the pipeline under the preset condition, measuring an ambient temperature; and according to the viscosity ratio and the ambient temperature, determining the smearing parameter using a table, a curve or a formula.

13. The smear control method of claim 1, wherein the reference fluid comprises a reference gas and a reference liquid when there is a liquid preserved in the pipeline, and the pressure of the reference fluid comprises a pressure of the reference gas and a pressure of the reference liquid.

14. The smear control method of claim 13, wherein the reference liquid is an isosmotic solution for the test sample.

* * * * *